US011576661B2

(12) United States Patent
Nino et al.

(10) Patent No.: US 11,576,661 B2
(45) Date of Patent: Feb. 14, 2023

(54) DISPOSABLE BIDIRECTIONAL RATCHET

(71) Applicant: ECA Medical Instruments, Newbury Park, CA (US)

(72) Inventors: John Nino, Los Angeles, CA (US); David Ivinson, Los Angeles, CA (US)

(73) Assignee: ECA Medical Instruments, Inc., Thousand Oaks, CA (US)

(*) Notice: Subject to any disclaimer, the term of this patent is extended or adjusted under 35 U.S.C. 154(b) by 0 days.

(21) Appl. No.: 15/172,041

(22) Filed: Jun. 2, 2016

(65) Prior Publication Data

US 2016/0278748 A1 Sep. 29, 2016

Related U.S. Application Data

(63) Continuation of application No. PCT/US2015/066489, filed on Dec. 17, 2015.

(Continued)

(51) Int. Cl.

*A61B 17/88* (2006.01)
*B25B 15/04* (2006.01)

(Continued)

(52) U.S. Cl.

CPC .............. *A61B 17/00* (2013.01); *A61B 17/56* (2013.01); *A61B 17/8875* (2013.01);

(Continued)

(58) Field of Classification Search

CPC ....... B25B 15/04; B25B 13/465; B25B 13/16; B25B 13/461; B25B 13/141;

(Continued)

(56) References Cited

U.S. PATENT DOCUMENTS 192,018 A * 6/1877 Rose ........................ B25B 15/04 81/32
2,772,763 A * 12/1956 Johnson ................ B25B 13/465 192/43.1

(Continued)

FOREIGN PATENT DOCUMENTS

WO 2014-116414 7/2014
WO 2014-164293 10/2014

OTHER PUBLICATIONS

Wikipedia. Dry Heat Sterilization. Online publication. http://en.wikipedia.org/w/index.php?title=Dry_heat_sterilization&oldid=845874657.*

(Continued)

*Primary Examiner* — Bryan R Muller
(74) *Attorney, Agent, or Firm* — Ferguson Case Orr Paterson

(57) ABSTRACT

A disposable bidirectional ratchet, which has a tubular hollow handle with an interior surface having teeth thereon; a toggle mounted movably within the handle; a knob connected to an end of the toggle moves the toggle inside the handle; a plurality of pins on another end of the toggle; a plurality of actuators each comprising: fingers, levers, toes and a head, and having a post guide formed therein; a plurality of posts affixed to a clutch; and, wherein the actuators are movable affixed to the clutch via the posts, and the pin position selects the direction of engagement via adjustment of the actuator position via applying force to the levers, which moves the lateral edges of the actuator towards or away from the teeth.

10 Claims, 15 Drawing Sheets

180 122 204 120 10 208 206 210 302 17 200 310 210 300 102 103 105 160 100 13 104 12 170 14 162 18

Related U.S. Application Data

(60) Provisional application No. 62/093,970, filed on Dec. 18, 2014.

(51) Int. Cl.
*B25B 23/14* (2006.01)
*A61B 17/00* (2006.01)
*A61B 17/56* (2006.01)
*F16H 31/00* (2006.01)

(52) U.S. Cl.
CPC ............ *B25B 15/04* (2013.01); *B25B 23/141* (2013.01); *F16H 31/005* (2013.01); *A61B 2017/0023* (2013.01); *A61B 2017/00407* (2013.01)

(58) Field of Classification Search
CPC ......... A61B 17/8875; F16D 1/00; F16D 1/12; F16D 1/16; A61L 2202/24
See application file for complete search history.

(56) References Cited

U.S. PATENT DOCUMENTS 3,290,969 A * 12/1966 Bergquist .............. B25B 13/465 81/63.1
3,330,316 A * 7/1967 Macneill ................. B25B 15/04 81/62
3,862,580 A * 1/1975 Pulles ..................... F16D 41/12 74/577 S
4,466,523 A * 8/1984 De Carolis ........... B25B 13/462 192/43.1
6,070,499 A * 6/2000 Wisbey ................. B25B 13/467 81/57.29
6,082,226 A * 7/2000 Lin ......................... B25B 15/04 192/43.1
6,793,900 B1 * 9/2004 Morck .................. A61L 2/0023 422/26
8,276,487 B2 10/2012 Wengreen et al.
8,865,064 B2 * 10/2014 Meier ....................... A61L 2/07 422/26
9,446,507 B2 * 9/2016 Nino ...................... A61B 90/03
2005/0204868 A1 9/2005 Liu
2006/0065080 A1 * 3/2006 Davidson ................ B25B 15/04 81/63
2010/0229694 A1 * 9/2010 Chen ..................... B25B 13/463 81/63.1
2010/0312140 A1 12/2010 Smith et al.
2013/0152746 A1 6/2013 Kerboul et al.
2013/0296888 A1 11/2013 Harper
2014/0224078 A1 8/2014 Kabo
2014/0266695 A1 * 9/2014 Addison ............. A61N 1/3787 340/539.12
2014/0276896 A1 9/2014 Harper
2015/0202018 A1 7/2015 Schaller et al.

OTHER PUBLICATIONS

Klein, Rolf. Laser Welding of Plastics. Berlin: Wiley-VCH, 2011. (Sample Chapter 1: https://application.wiley-vch.de/books/sample/3527409726_c01.pdf).*
Wikipedia. Dry Heat Sterilization. Online publication. http://en.wikipedia.org/w/index.php?title=Dry_heat_sterilization&oldid=845874657 (Year: 2018).*
Klein, Rolf. Laser Welding of Plastics. Berlin: Wiley-VCH, 2011. (Sample Chapter 1: https://application.wiley-vch.de/books/sample/3527409726_c01.pdf) (Year: 2011).*
ALFA Medical Equipment, Autoclave Time Temperature Pressure Chart, 1995, https://sterilizers.com/autoclave-time-temperature-pressure-chart.html (Year: 1995).*
ALFA Medical Equipment, Alfa's Profile, 1995, http://www.alfa-medical.com/ (Year: 1995).*
International Patent Application No. PCT/US2015/066489; Int'l Preliminary Report on Patentability; dated Jun. 29, 2017; 8 pages.
International Search Report and Written Opinion dated Apr. 1, 2016, issued in International patent application PCT/US2015/066489 filed Dec. 17, 2015.
European Patent Application No. 15871117.6; Extended Search Report; dated Jun. 28, 2018; 7 pages.

* cited by examiner

DISPOSABLE BIDIRECTIONAL RATCHET

CROSS-REFERENCE TO RELATED APPLICATIONS

This patent application is a Continuation of International patent application PCT/US2015/066489 filed Dec. 17, 2015, and US Provisional patent application 62/093,970 filed Dec. 18, 2014, the disclosures of which are incorporated by reference in their entirety.

BACKGROUND

Field

This disclosure relates to a disposable limited use ratchet.

General Background

Traditional ratchet devices used in the medical industry require repeat sterilization, are susceptible to coating or caking with medical waste, and may fall out of specification and fail to operate over time.

Human bone, tissue, blood and other fluids are frequently present during surgical procedures. These materials may be medical waste. Medical waste includes: "Any discarded biologic product such as blood or tissue removed from operating rooms, morgues, laboratories, or other medical facilities. The term may also be applied to bedding, bandages, syringes, and similar materials that have been used in treating patients and to animal carcasses or body parts used in research. Medical waste is regulated at the state and local levels. "Mosby's Medical Dictionary, 8th edition. © 2009, Elsevier.

Medical waste is regulated and needs to be properly disposed of. Part of the disposal process is the collection of such medical waste.

SUMMARY

Briefly stated, the disposable bidirectional ratchet using a finger, toe and tooth system provides a compact, novel limited-use device, which obviates the need for repeat sterilization during the predetermined maximum number of use cycles, thusly obviating the shortfalls of prior medical bidirectional ratchets.

Disclosed herein are aspects of methods, systems and disposable bidirectional ratchet devices including a hollow handle with an interior surface having teeth thereon; a toggle within the handle; a knob that moves the toggle; a plurality of pins on an end of the toggle; a plurality of actuators, each having fingers, levers, toes and a head having a post guide formed therein; a plurality of posts affixed to a clutch; and, wherein the actuators are movably affixed to the clutch via the posts, and the pin position selects the direction of engagement via adjustment of the actuator position via applying force to the levers, which moves the lateral edges of the actuator towards or away from the teeth. In some instances the finger of the actuator comprises an obtuse side, an engaging side, and a neutral side.

Disclosed herein are aspects of methods, system bidirectional ratchet devices including a hollow handle with an interior surface having teeth thereon; a toggle within the handle; a knob that moves the toggle; a plurality of pins on an end of the toggle; a plurality of actuators, each having fingers, levers, toes, and a head having a post guide formed therein; a plurality of posts affixed to a clutch; and, wherein the actuators are movably affixed to the clutch via the posts, and the pin position selects the direction of engagement via adjustment of the actuator position via applying force to the levers, which moves the lateral edges of the actuator towards or away from the teeth, the fingers, levers, toes and a head are a unitary plastic part; and, the levers deform and act as springs applying adequate pressure to the fingers to have the fingers follow the contours of the teeth.

Disclosed herein are aspects of methods, systems and disposable bidirectional ratchet devices including a hollow handle with an interior surface having teeth thereon; a toggle within the handle; a knob that moves the toggle; a plurality of pins on an end of the toggle; a plurality of actuators, each having fingers, levers, toes and a head having a post guide formed therein; a plurality of posts affixed to a clutch; and, wherein the actuators are movably affixed to the clutch via the posts, and the pin position selects the direction of engagement via adjustment of the actuator position via applying force to the levers, which moves the lateral edges of the actuator towards or away from the teeth, the fingers, levers, toes and a head are a unitary plastic part; the levers deform and act as springs applying adequate pressure to the fingers to have the fingers follow the contours of the teeth; and the levers deform and act as springs applying adequate pressure to the fingers to have the fingers follow the contours of the teeth.

Disclosed herein are aspects of methods, systems and disposable bidirectional ratchet devices including a hollow handle with an interior surface having teeth thereon; a toggle within the handle; a knob that moves the toggle; a plurality of pins on an end of the toggle; a plurality of actuators, each having fingers, levers, toes and a head having a post guide formed therein; a plurality of posts affixed to a clutch; and, wherein the actuators are movably affixed to the clutch via the posts, and the pin position selects the direction of engagement via adjustment of the actuator position via applying force to the levers, which moves the lateral edges of the actuator towards or away from the teeth, the fingers, levers, toes and a head are a unitary plastic part; the levers deform and act as springs applying adequate pressure to the fingers to have the fingers follow the contours of the teeth; and, wherein the levers fail to keep adequate pressure on the finger associated therewith for the fingers to consistently follow the teeth after about 600 cycles.

In one or more of the above exemplary implementations wherein a disposable bidirectional ratchet has the pins in a first location, where they apply a force to the levers such that the actuators pivot into a first position, and when the ratchet is turned in a first direction, rotational force is applied in the opposite direction.

In one or more of the above exemplary implementations wherein the disposable bidirectional ratchet pins are in a second location, where they apply a force to the levers such that the actuators pivot into a second position, and when the ratchet is turned in a second direction, rotational force is applied in the opposite direction.

In one or more of the above exemplary implementations of the disposable bidirectional ratchet the engaging side of the finger of the actuator abuts at least one of the teeth, and a toe not adjacent to the engaging side abuts a rib of the clutch. And, in some instances when the ratchet is turned in an opposite direction, the finger slides over the tooth without catching. In one or more of the above exemplary implementations of the disposable bidirectional ratchet the pins are configured to apply a force to the levers such that once the finger slides over the tooth, the engaging side is in contact with that tooth. In one or more of the above exemplary implementations of the disposable bidirectional ratchet the pins are in a third location, where the pins do not apply a force to the levers.

In one or more of the above exemplary implementations of the disposable bidirectional ratchet the include a handle having a passage extending therethrough; the passage defining an internal surface, wherein the inner surface has a plurality of protrusions; a neck configured to attach to a tool; a clutch having at least one post; at least one actuator wherein the actuator comprises a head having a post guide therein, a finger, a toe, and a lever; a toggle portion having a plurality of pins, wherein the toggle is moved by a knob; wherein the actuator is movably attached to the post via the post guide; wherein the pins are configured to be moved and apply force to the lever of the actuator; and wherein the actuator is configured to engage a first protrusion, engage a second protrusion, or engage no protrusions in response to the force applied by the pin on the lever or in the absence of force.

In one or more of the above exemplary implementations of the disposable bidirectional ratchet a method of ratcheting with a unitary plastic lever is taught, the method including placing a clutch inside a hollow handle with an interior surface having teeth thereon; forming a plurality of posts affixed to the clutch; placing a plastic actuator, each having fingers, levers, toes, and a head, movably on each post; placing a toggle within the handle connected to a knob that moves the toggle and selects a direction of engagement; wherein the actuator applies force to the levers, which moves the lateral edges of the actuator towards or away from the teeth; and, wherein the levers are a unitary part of the actuator, which deform during use to provide spring force for a limited number of actuations.

In one or more of the above exemplary implementations of the disposable bidirectional ratchet a method of ratcheting with a unitary plastic lever is taught, the method including placing a clutch inside a hollow handle with an interior surface having teeth thereon; forming a plurality of posts affixed to the clutch; placing a plastic actuator, each having fingers, levers, toes, and a head, movably on each post; placing a toggle within the handle connected to a knob that moves the toggle and selects a direction of engagement; wherein the actuator applies force to the levers, which moves the lateral edges of the actuator towards or away from the teeth; and, wherein repeated deformation of levers over 600 cycles will cause one or more levers to fail to provide adequate force to a finger to one of engage and disengage teeth.

DRAWINGS

The above-mentioned features of the present disclosure will become more apparent with reference to the following description taken in conjunction with the accompanying drawings, wherein like reference numerals denote like elements, and in which.

Figure 9:
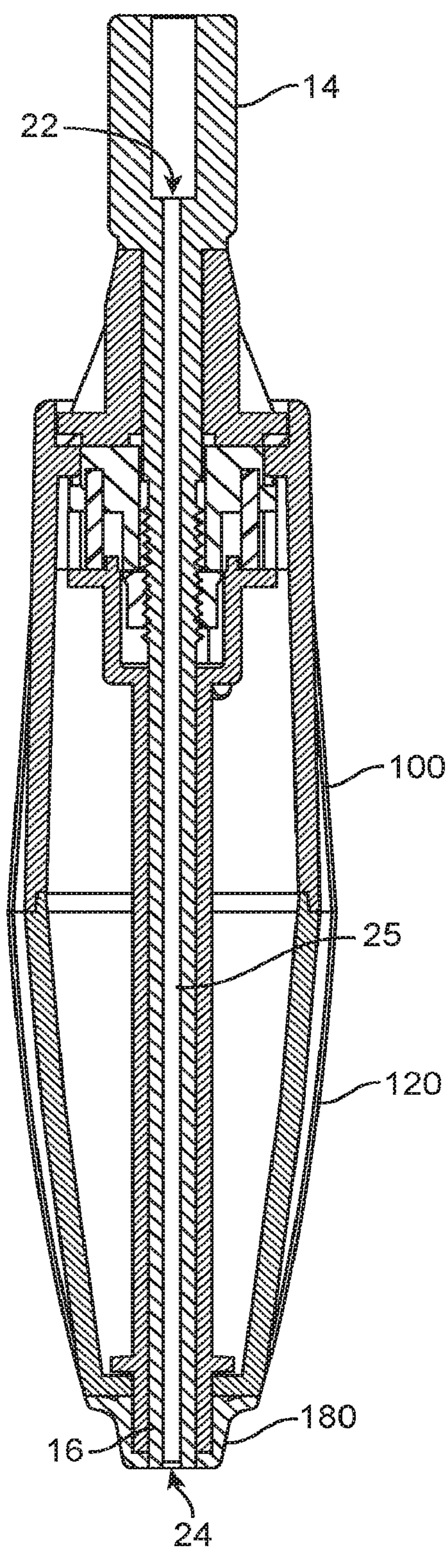
Figure 10:
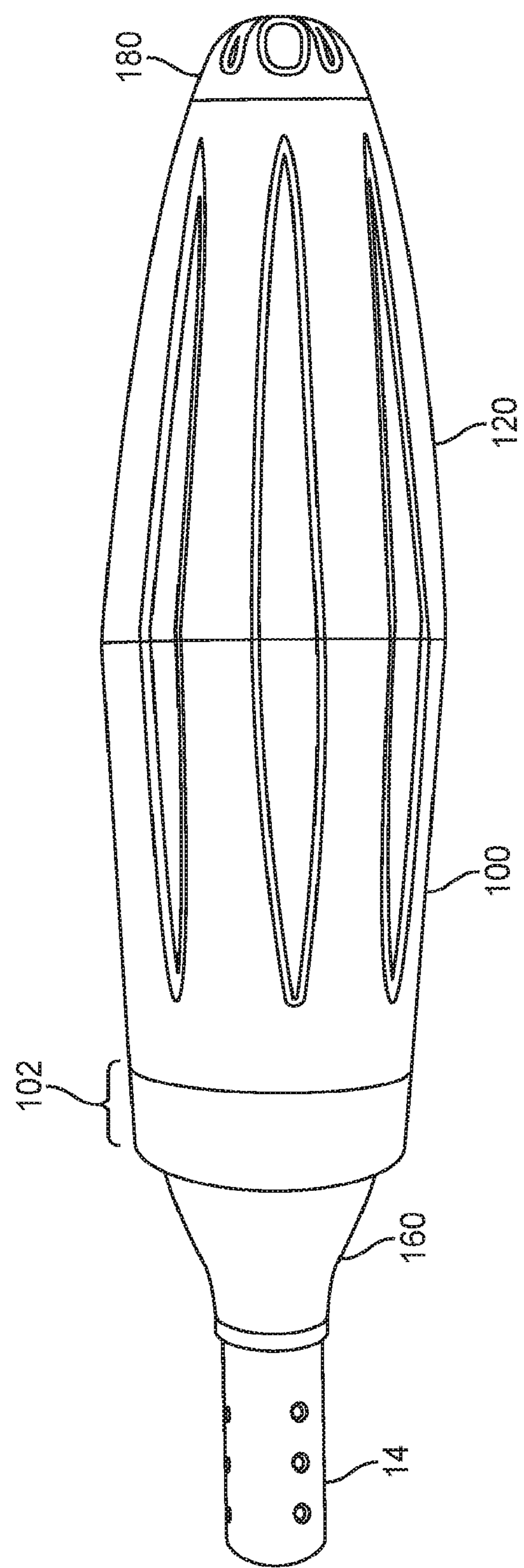

FIGS. 8A-D show operation of the actuators within the handle;

FIG. 9 shows a cut-away assembled view of a cannulated device; and,

FIG. 10 shows an assembled device.

While the specification concludes with claims defining the features of the present disclosure that are regarded as novel, it is believed that the present disclosure's teachings will be better understood from a consideration of the following description in conjunction with the appendices and figures, in which like reference numerals are carried forward. All descriptions and callouts in the Figures are hereby incorporated by this reference as if fully set forth herein.

FURTHER DESCRIPTION

According to one or more exemplary implementations, FIGS. 1-10 illustrate aspects of devices, systems, and methods of ratcheting, providing ratcheting and disposable ratchets.

Figure 1A:
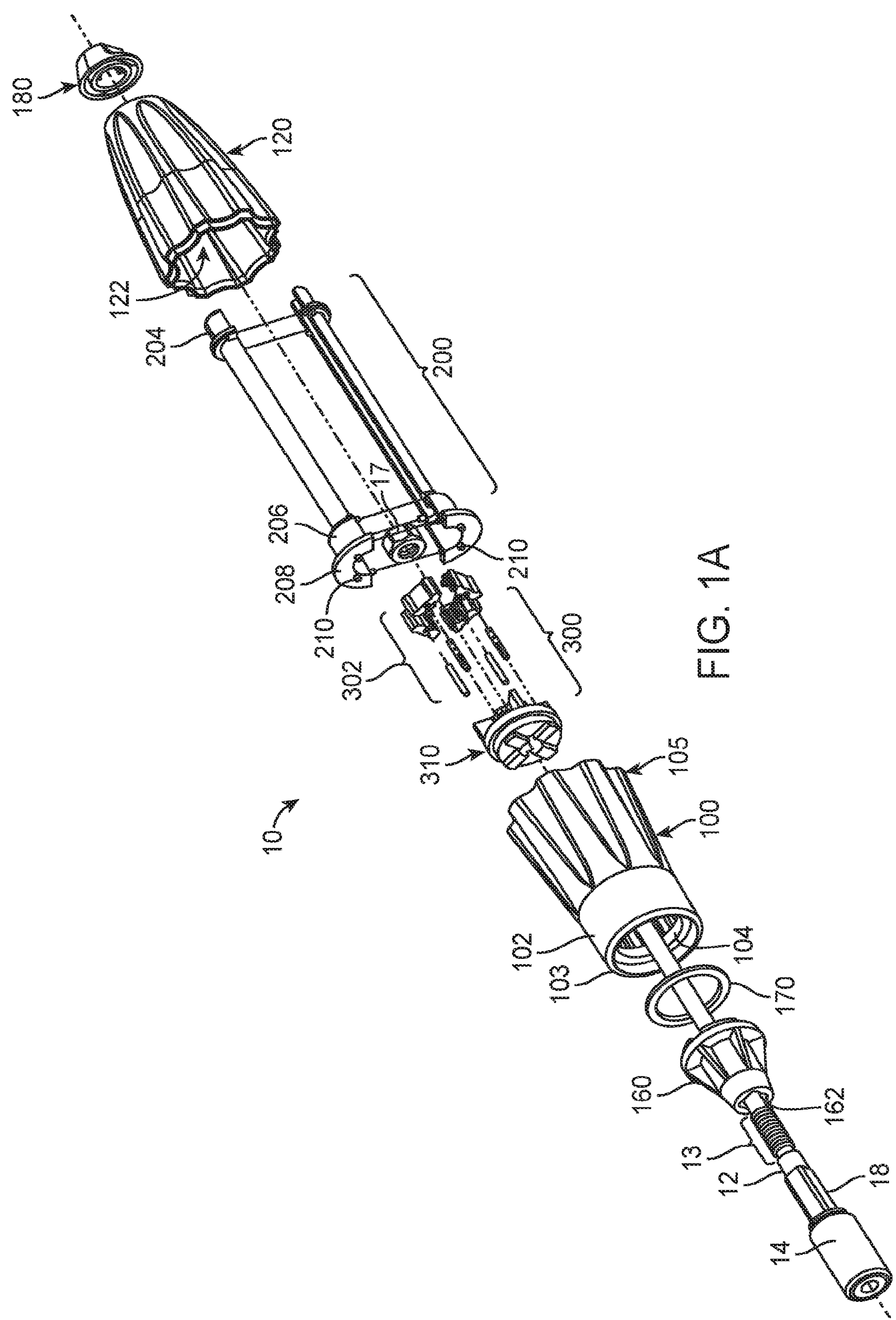
FIGS. 1A and 1B show assembly views of aspects of a disposable bidirectional ratchet.
Figure 1B:
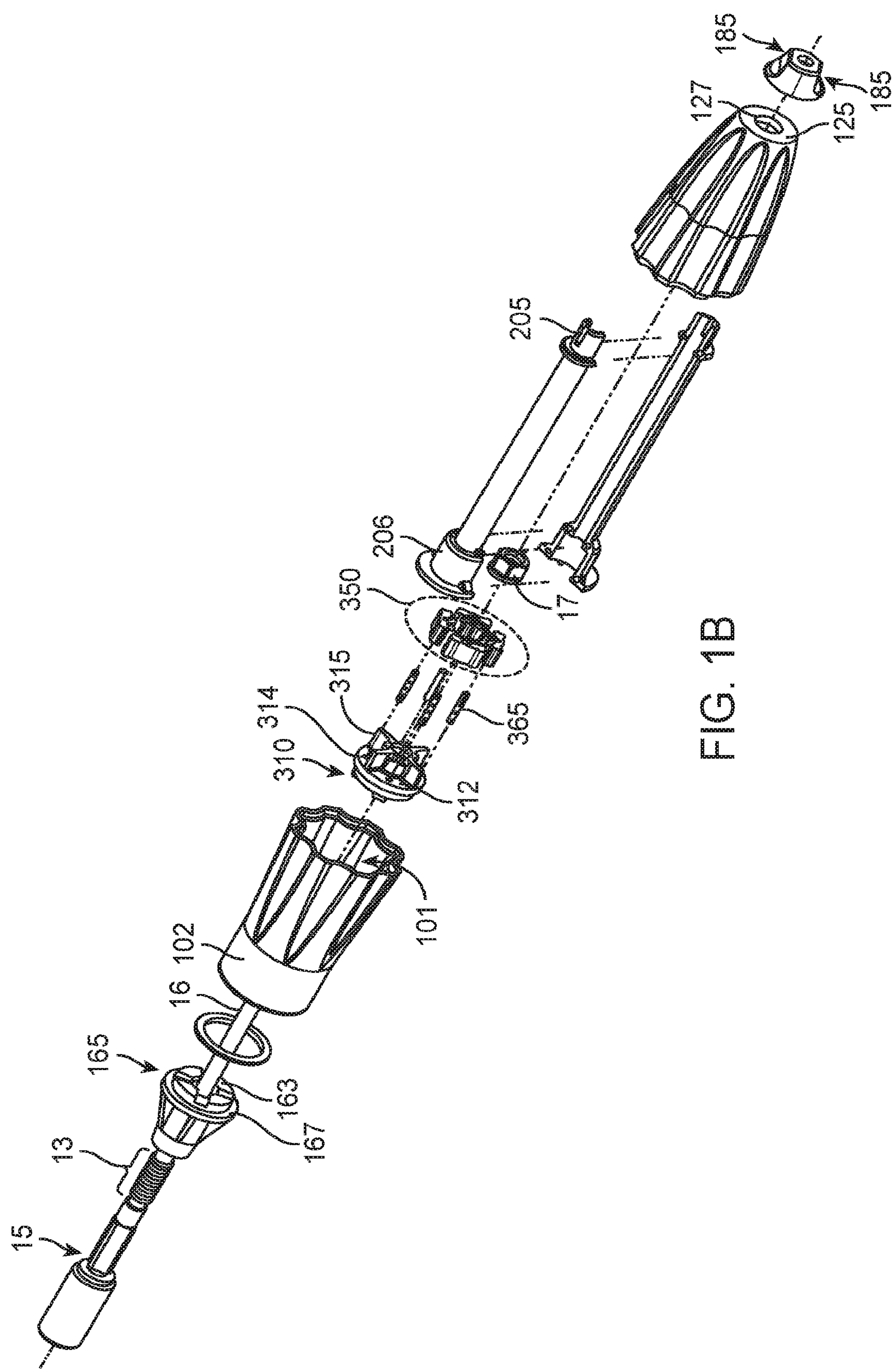
Figure 2:
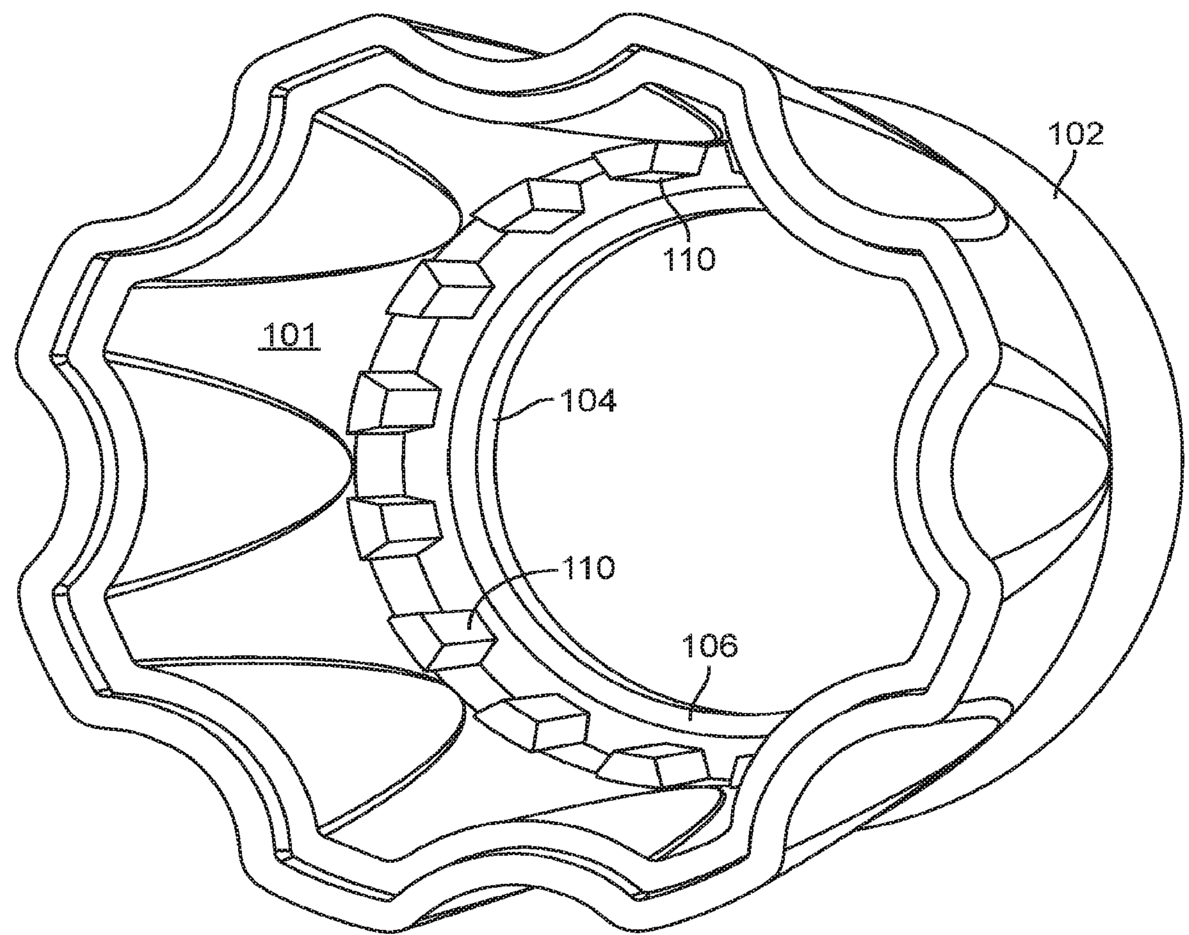
FIG. 2 shows an interior view of the body.
Figure 3:
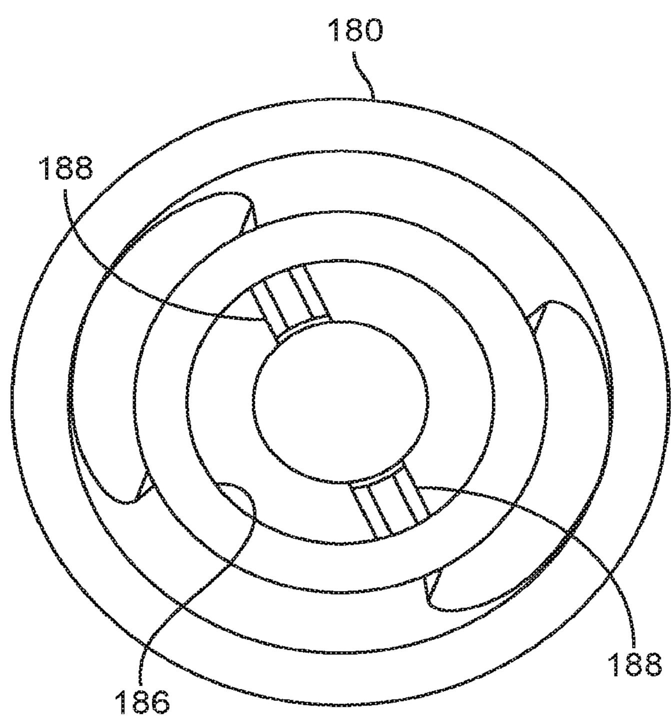
FIG. 3 shows the interior view of the knob.
Figure 4:
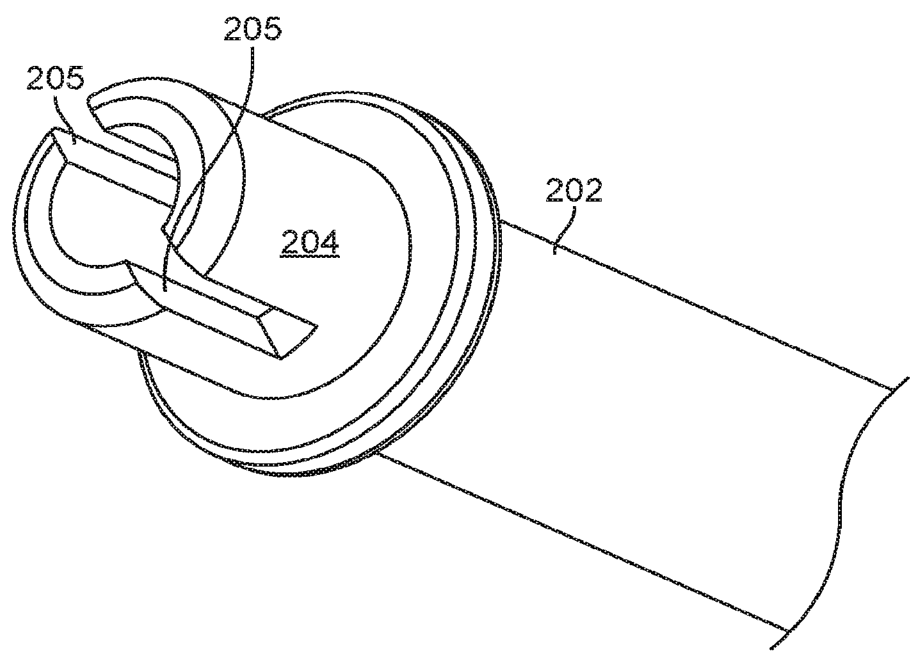
FIG. 4 shows the proximal end of the toggle.
Figure 5:
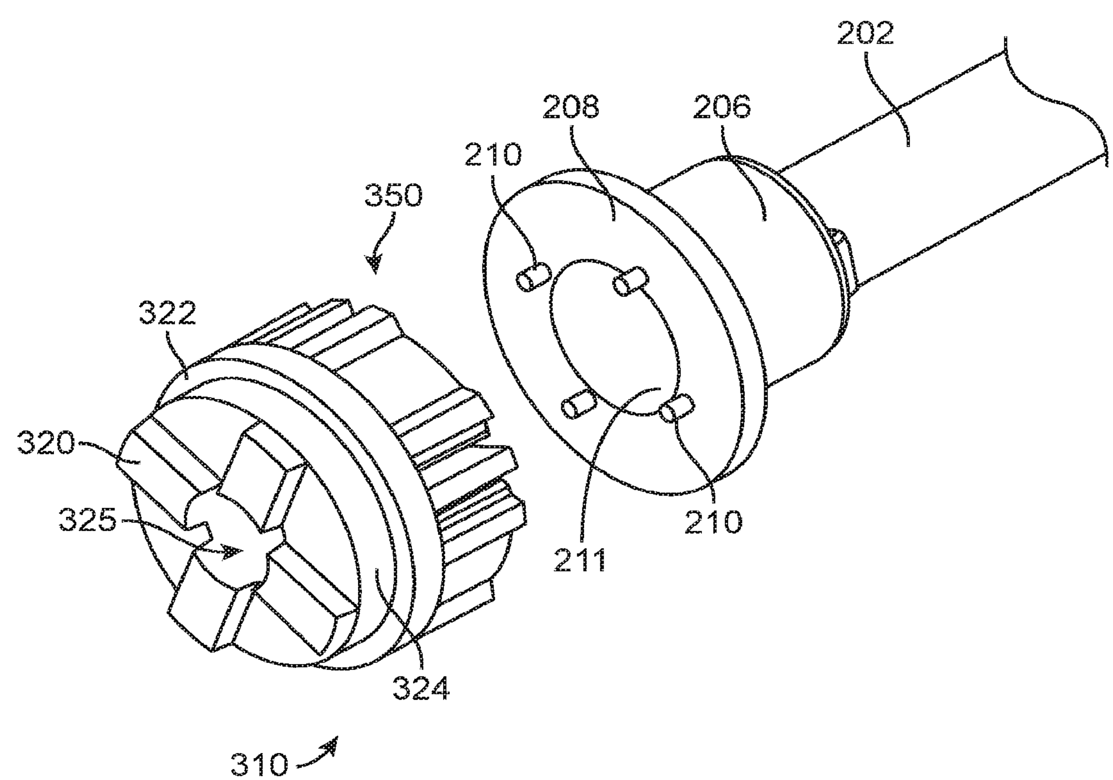
FIG. 5 shows the distal end of the toggle and the clutch with actuators.

FIGS. 1A and 1B illustrate assembly views of disposable bidirectional ratchet 10. The device has a handle which contains a ratcheting mechanism, a toggle to switch ratcheting directions, and a shaft with tool to use with instruments used in medical procedures. The handle supports a shaft 12 that has a partially-threaded portion 13, a proximal end 15, and a distal end 16. The shaft is connected to a tool 14. A nut 17 or other fastener connects the shaft to an internal selecting mechanism or toggle.

FIGS. 1A-10 illustrate aspects of disposable bidirectional ratchets. The handle is made of a tubular front body 100 connected to a tubular back body 120. The front body 100 has an interior wall 101, an open end 102 forming a receiving guide 103, an internal annular wall 104 inside the receiving guide and an open back end 105 and having a clutch flange 106 and teeth 110 extending periodically from the interior wall 101. The back body 120 has an open front end 122 and a back end 24, which is partially closed 125, and has a back body aperture 127 fluidly connecting the exterior and interior of the back body. A rotatable extended neck 160 has an aperture 162 on one end, which affixes the non-round shaft portion 18, fluidly connecting it to the inside of the body, and a first drive connection 163 on its back side 165. An annular ring 167 is formed around the drive connection. During assembly, a plastic washer 170, such as PTFE or polypropylene, is interposed between the annular ring and the internal annular wall 104. A toggle knob 180 with finger grabs 185 (for rotating the knob) is connected to the internal ratcheting structures through the back body aperture 127. Inside the knob is an annular wall forming a toggle guide 186 and ribs 188 which mate with the toggle assembly 200.

Inside the handle are toggle assembly 200, the ratcheting assembly 300 and the actuator system 302. The toggle assembly 200 has a hollow elongated member 202 with a distal end 204 with rib catches 205 formed therein and a proximal end 206 with a flat face 208 supporting drive pins 210. A fluid connection 211 is formed from the distal end to the proximal end. The rib catches 205 mate with the ribs 188 inside the knob 180 and can be used to rotate the toggle, thereby rotating the drive pins, which in turn direct the positive direction of the ratcheting device. The proximal end 206 also forms a receptacle for the nut 17, which mates with the threaded portion 13 of the shaft. The shaft threaded on to the nut holds together the two body halves and nose.

The ratcheting assembly 300 has two subparts, which are the actuator system 302 and the clutch 310. The back side of the clutch 312 provides post connection guides 314 and clutch ribs 315. A second drive connection 320, which mates with the first drive connection 163 of the neck 160, is on the front side of the clutch. Also on the front side is an annular ring 322, which surrounds a raised wall 324, which passes through the receiving guide 103. The annular ring 322 uses the clutch flange 16 as a bearing plate, which it rotates against. A shaft guide 325 forms a passageway for the shaft through the ratcheting assembly. An array of actuators 350 are connected to the clutch's back side 312 via posts 365.

Figure 6A:
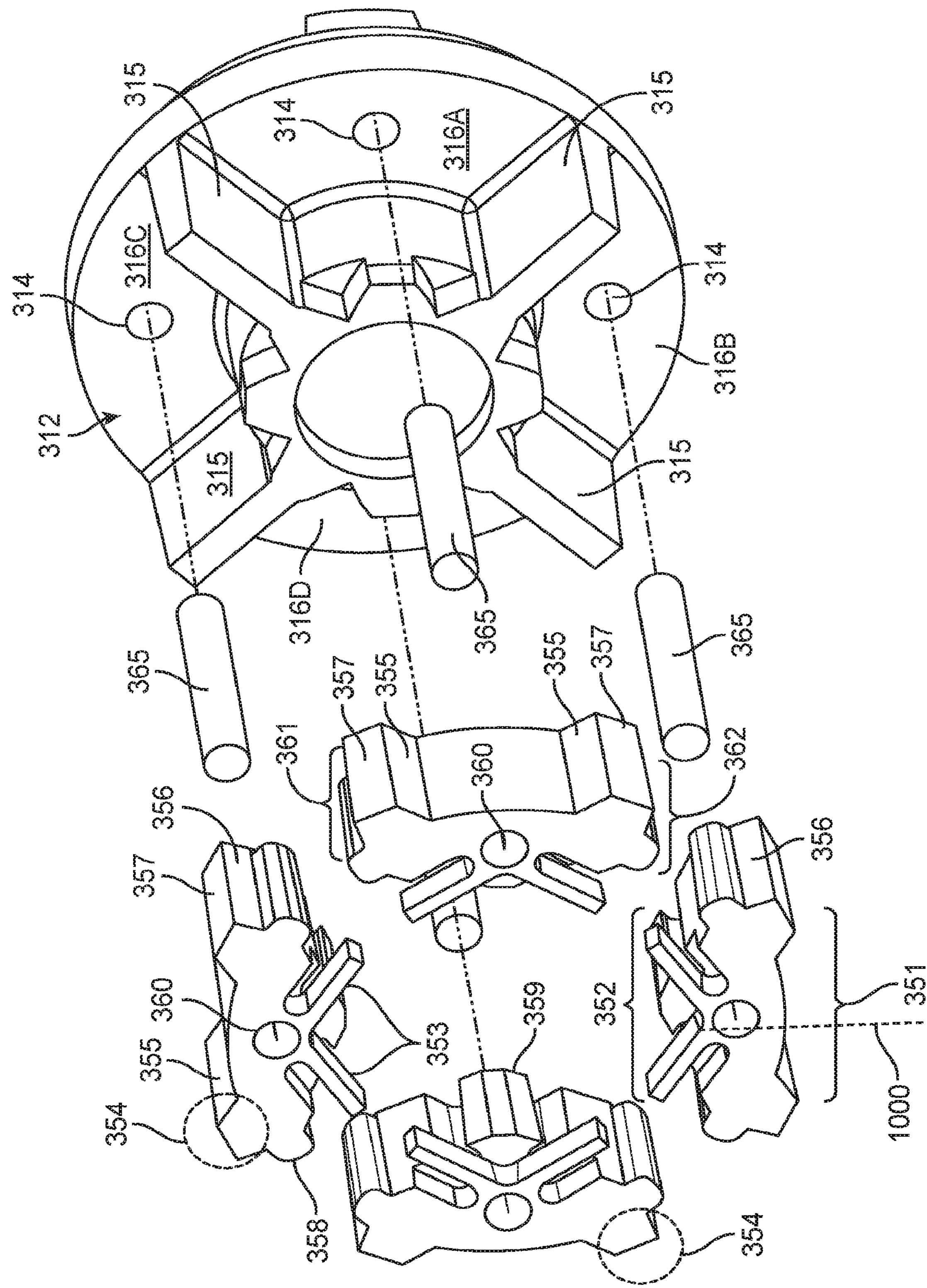
FIGS. 6A and 6B show an assembled and disassembled ratchet assembly.
Figure 6B:
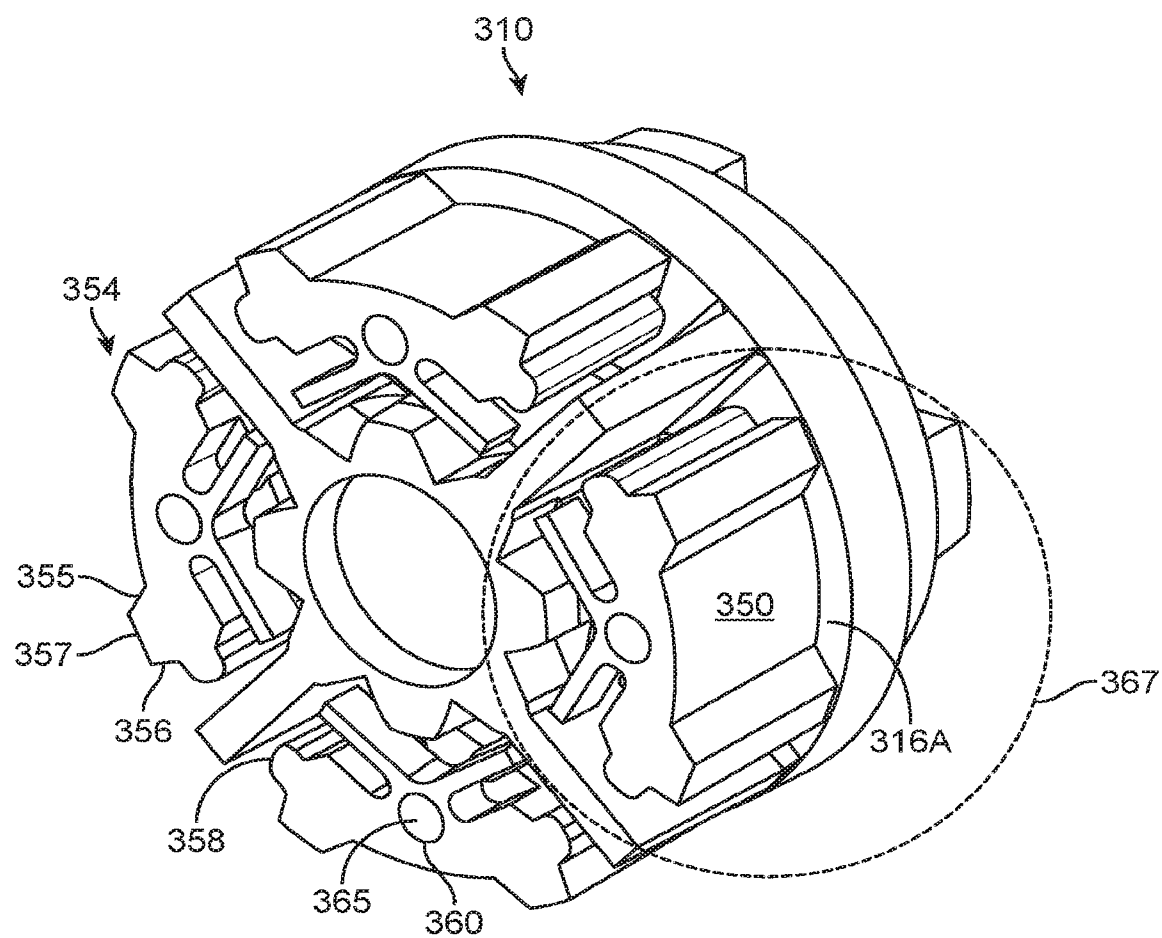

FIGS. 6A and 6B show the assembly of the ratcheting assembly. The ribs 315 extending from the clutch backside face 312 separate the ratcheting assembly into four compartments 316A-D each bordered by two ribs 315 and having a post connection guide 314. Each actuator 350 fits on a post 365, which is mounted in a post connection guide 314. Actuators are formed of plastic, resin, or other non-metal composite and have a dorsal side 351 and a ventral side 352. On the ventral side are two lever arms 353. The lever arms are spring members that have a limited life cycle; they are formed as an integral part of the actuator. The limited number of actuations allows the lever arms 353 to be unitary with the actuator 350. The lever arms are susceptible to failure if they are exposed to the heat of sterilization, such as an autoclave, accordingly when used in medical procedures the device utilizing the levers should be disposed of after use and not subjected to the heat of sterilization. Laterally, each actuator has a finger 354 and a toe 358. Each finger has three sides: an obtuse side 355, which is positioned toward the centerline 1000; an engaging side 356, which is furthest from the centerline; and a neutral side 357 between the obtuse and engaging sides. On the ventral side is a head 359, and through the actuator is a pivot guide 360, via which the actuator movably mates with the post 365. Those of ordinary skill in the art will recognize that although the illustrations show a four compartment (316A-D) clutch back, that number is not a limitation, and there could be fewer or more compartments. An actuator mounted in a compartment may also be referred to as an actuation module 367. The actuators 350 partially rotate around the post, whereby the first lateral side 361 or the second lateral side 362, and the finger and toe associated therewith, is engaged with the teeth 110. During transition from positive rotation clockwise to positive rotation counterclockwise, neither lateral side is engaged (see FIG. 8B and 8C).

Figure 7:
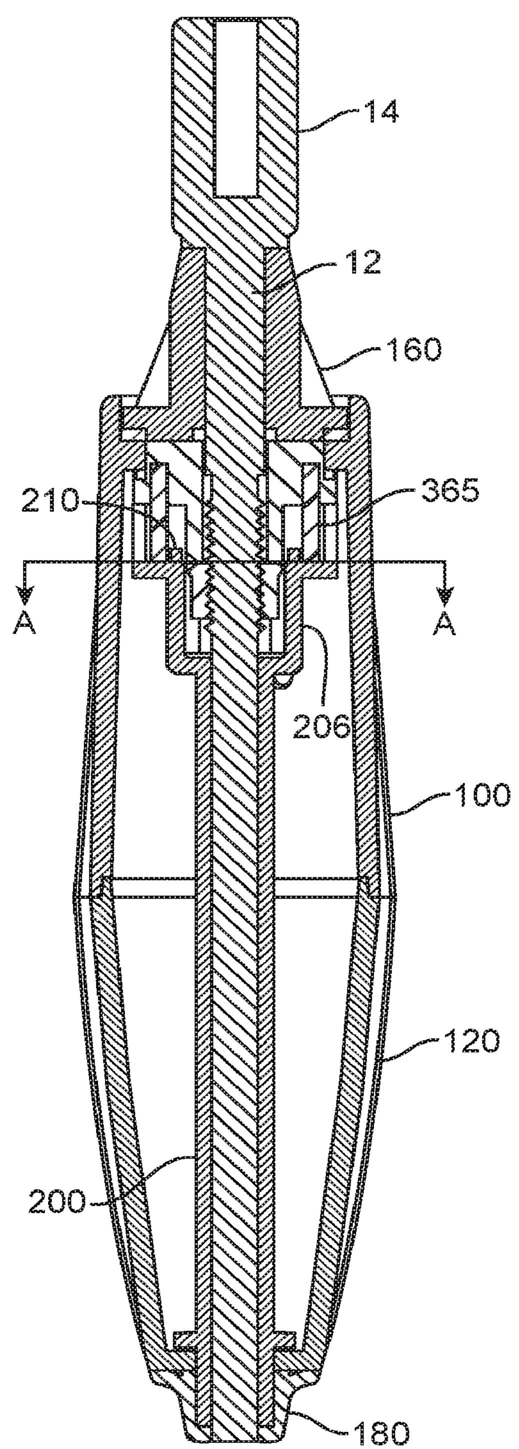
FIG. 7 shows a cut-away assembled view of a non-cannulated device.
Figure 8A:
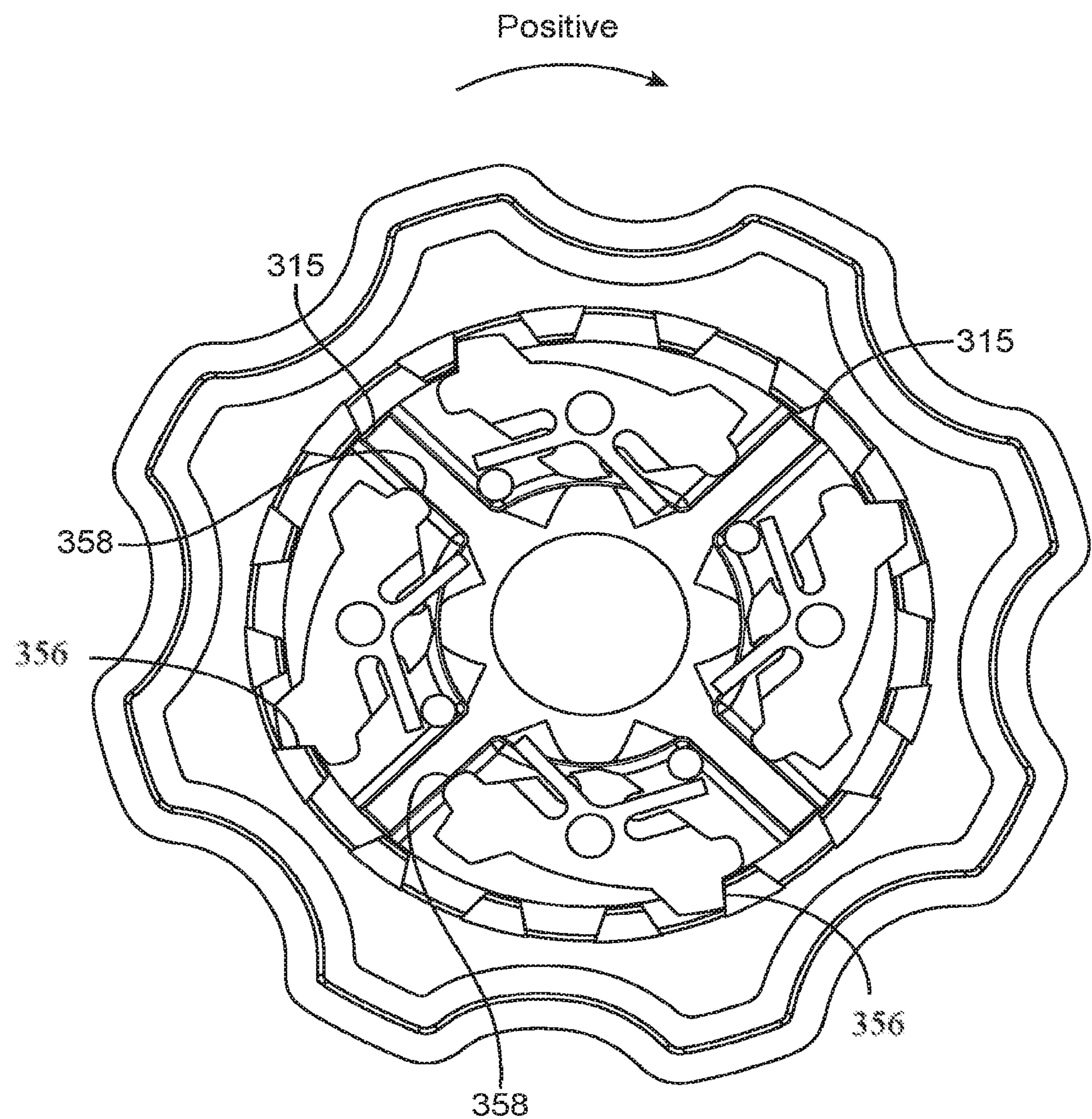
Figure 8B:
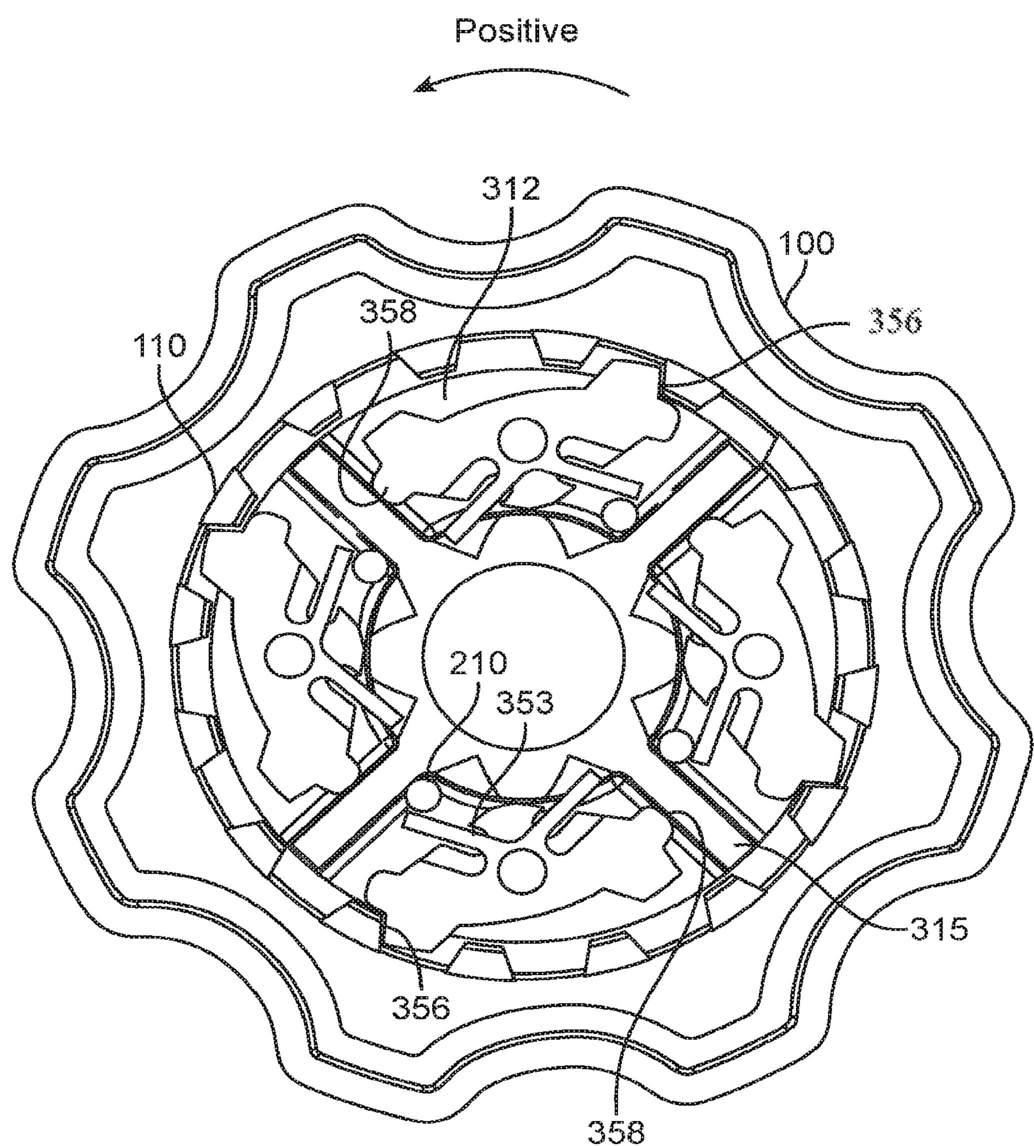
Figure 8C:
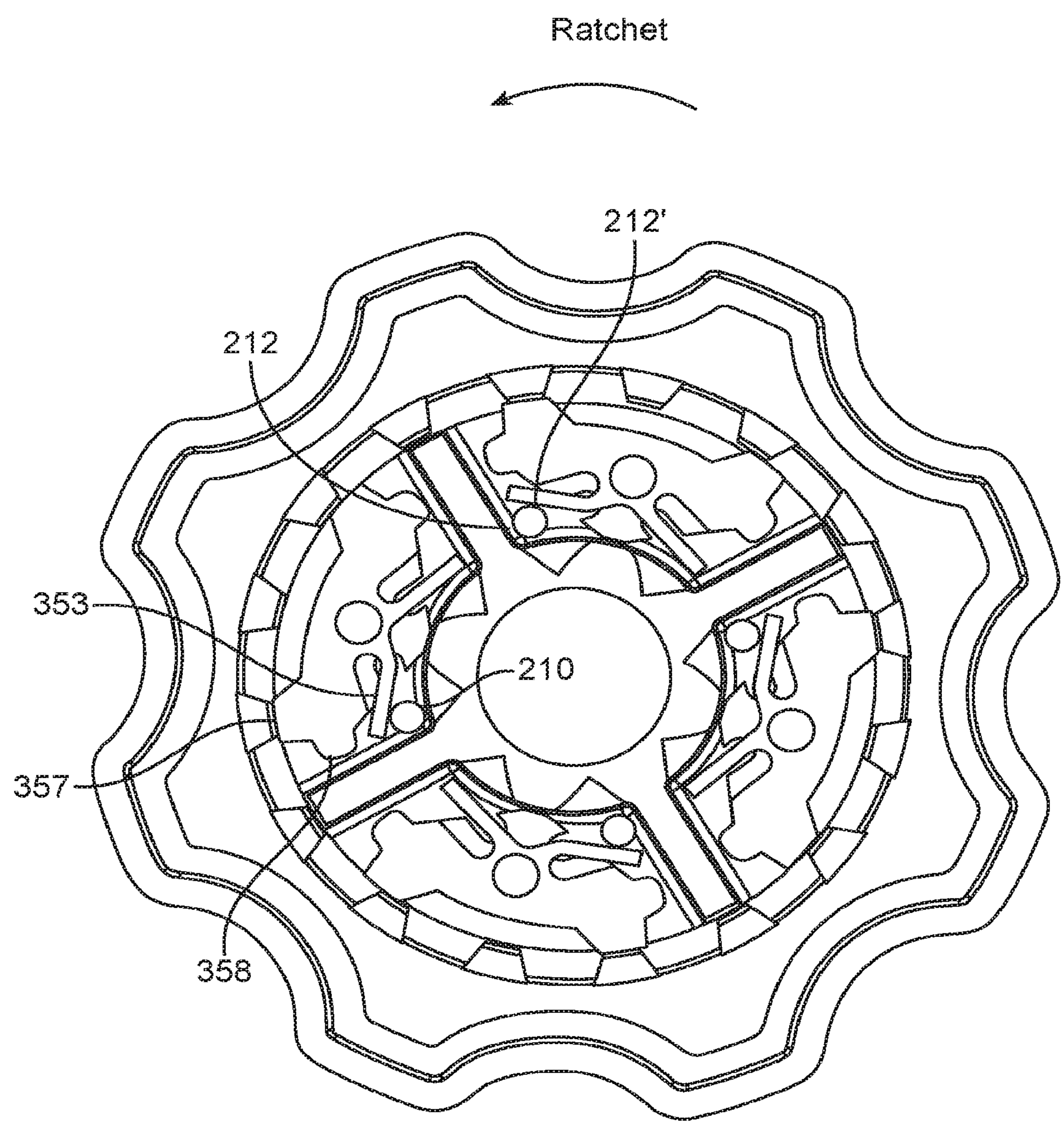
Figure 8D:
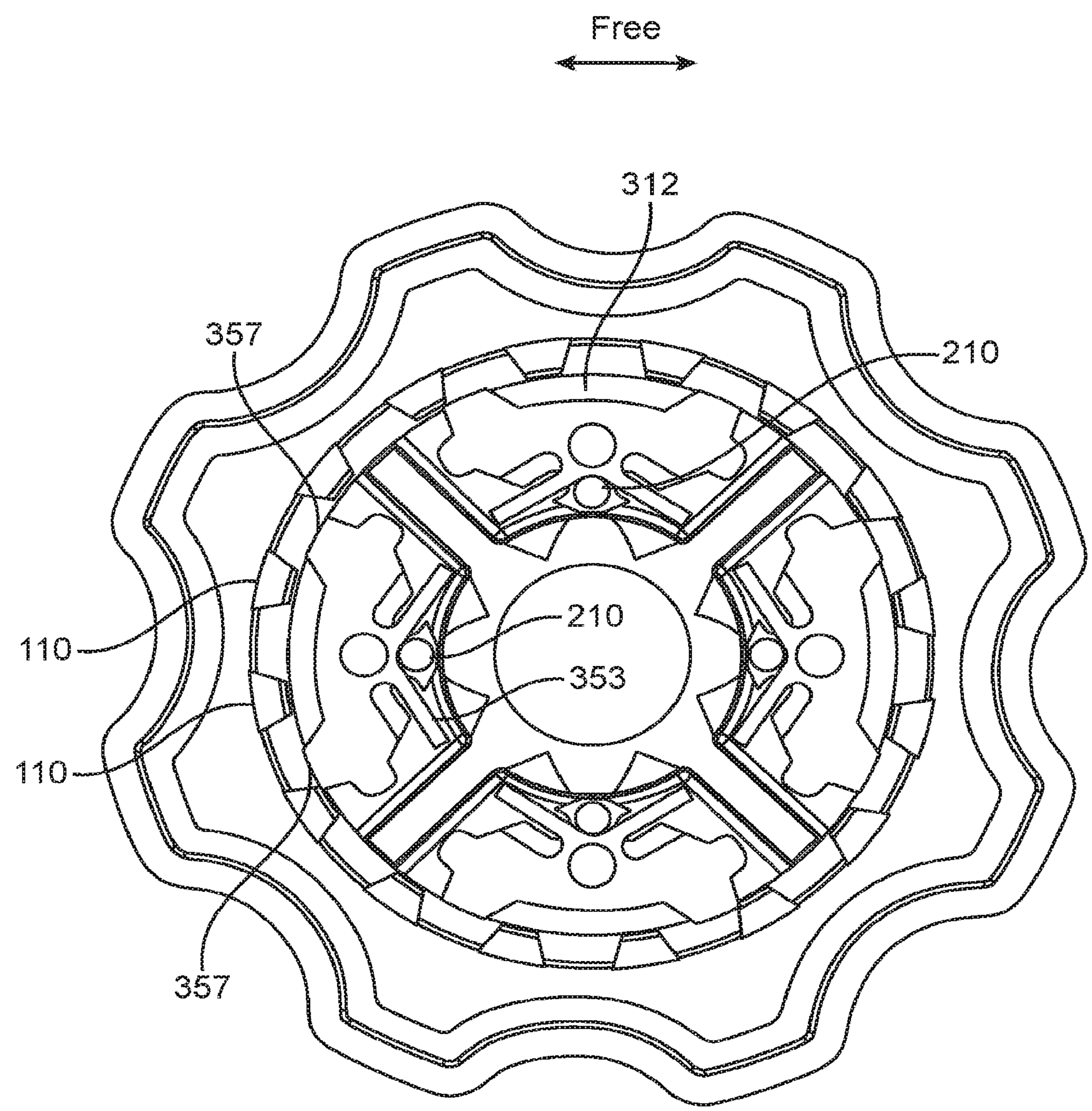

FIG. 7 shows a cut away view of disposable bidirectional ratchet devices with a solid shaft.

FIGS. 8A-8D show a cut away view of FIG. 7 along the line of "A"-"A" movement of the actuators via the drive pins 210. The drive pins are adjusted via the toggle 200, which is moved via the toggle knob 180. Moving the drive pins 210 (via rotation of the knob) applies force to the levers 353, which are temporarily deformed, and which respond with a spring action to pivot the actuator from first position "A" to neutral position "B" to a second position "C". The pins are rotated via the knob 180. A fourth pin position is the result of turning the handle of the ratchet opposite the positive rotation. In that mode, the pins 210 move from a first position 212 to a second position 212', which is slightly away from the clutch ribs 315. That movement deforms one of the pair of levers 353 and keeps pressure on the finger 354, which then follows the contour of the teeth 110 without catching. The deformation of the lever allows it to act as a catch and a spring at the same time. The deformation over time will cause the lever to fail to actuate consistently during use. It is a functional limitation of some exemplary implementations that the lever arms, during uses, degrade and are unable to perform consistently. Testing to failure has shown that lever arms begin to fail to actuate consistently after approximately 600 cycles. The foregoing is intended to be the antecedent basis for a negative claim limitation. The Plastic lever arms are cost saving and space saving as integral parts of the plastic actuator, however, they are frangible and will lose function over uses. It is preferred that they function consistently for about 400 cycles, it is more preferred that the function consistently for about 500 cycles and it is most preferred that they function consistently for about 600 cycles. Consistent functions means a lever keeps adequate pressure on the finger 354 associated therewith wherein the finger follows the contour of the teeth 110 during the cycle.

A cycle corresponds to an approximate ½ turn (about a 180 degree rotation) of the handle during use. The position of the pins 210 can be seen relative to the back of clutch 312 and the clutch ribs 315. The pins 210 position the actuators. During use, the teeth 110 on the inside of the handle act as catches for the engaging side 356 of each finger. The pins 210 drive the actuators to one of a first, neutral and second position, and those positions correspond to placement of the teeth and fingers in an engagement for clockwise or counterclockwise movement. During usage, on each actuator 350, the toes 358 furthest from the engaging side 356, which is against a tooth 110, abuts the rib 315 of the clutch, thereby acting as a buttress for the actuator as the engaging side 356 and tooth 110 apply force to the neck 160 and the shaft 12. When adjusting the actuators, the obtuse side 355 does not catch the teeth 110 and slides over them allowing the handle to rotate/ratchet without engagement. By reversing handle direction, the engaging side 356 is then engaged with the teeth 110. Drive pins 210 can place the actuators in a neutral position or select a clockwise or counterclockwise direction of engagement, wherein the device, when turned, will apply rotational force in an opposite direction. Knob 180 is used to select the pin position and the direction of positive rotation and ratchet, as well as the position of free movement if it is moved in-between positions.

FIG. 9 shows a cut away view of a disposable bidirectional ratchet device. FIG. 8 is a device with a solid shaft. FIG. 9 shows a cannulated shaft 12 having a first opening 22 at the proximal end 15, wherein the handle supports a shaft 12, which has a partially threaded portion 13 and is connected to a tool 14 at its proximal end 15, cannulated shaft 12 further having a second opening 24 at the distal end 16 of the shaft. A passageway 25 runs between the first and second openings, wherein a guide wire may be passed, or fluid added or evacuated, or viewing devices such a fiber optics may be inserted, or illumination devices, laser device, or radio frequency devices may be added or passed.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure, both independently and as an overall system, and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard, it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "comprise", or variations such as "comprises" or "comprising", are intended to imply the inclusion of a stated element or step or group of elements or steps, but not the exclusion of any other element or step or group of elements or steps.

Such terms should be interpreted in their most expansive forms so as to afford the applicant the broadest coverage legally permissible.

The invention claimed is:

1. A disposable bidirectional ratchet designed to be disposed of after use and not sterilized, the bidirectional ratchet comprising:

a handle comprising a tubular front body affixed to a tubular back body;

the tubular front body comprising an interior wall, said interior wall comprising teeth extending periodically from the interior wall;

a toggle within the handle, said toggle comprising a hollow elongated member;

a knob that moves the toggle;

a plurality of pins with longitudinal axes parallel to a longitudinal axis of said handle on an end of the toggle;

a plurality of actuators, each actuator comprising:

fingers, levers, toes, a head, and a post guide formed in the actuator;

a plurality of posts affixed to a clutch; and, wherein the actuators are movably affixed to the clutch via the posts, and the pin position selects the direction of engagement via adjustment of the actuator position via applying force to at least one of the levers of each actuator, which moves each of the fingers of each actuator towards or away from each of the teeth.

2. The disposable bidirectional ratchet according to claim 1, wherein each finger of each actuator comprises an obtuse side, an engaging side, and a neutral side.

3. The disposable bidirectional ratchet according to claim 2, wherein when the pins are in a first location, the pins apply a force to at least one of the levers such that each of the actuators pivot into a first position, and when the handle is turned in a first direction, rotational force is applied in the opposite direction by the engaging side of each of the actuators.

4. The disposable bidirectional ratchet according to claim 2, wherein when the pins are in a second location, the pins apply a force to at least one of the levers such that each of the actuators pivot into a second position, and when the handle is turned in a second direction, rotational force is applied in the opposite direction by the engaging side of each of the actuators.

5. The disposable bidirectional ratchet according to claim 3, wherein the engaging side of at least one of the fingers of each actuator abuts at least one of the teeth, and a toe not adjacent to the engaging side abuts a rib of the clutch.

6. The disposable bidirectional ratchet according to claim 4, wherein the engaging side of at least one of the fingers of each actuator abuts at least one of the teeth, and a toe not adjacent to the engaging side abuts a rib of the clutch.

7. The disposable bidirectional ratchet according to claim 5, wherein when the handle is turned in a direction opposite the first direction, each finger slides over the at least one of the teeth without catching.

8. The disposable bidirectional ratchet according to claim 6, wherein the pins are configured to apply a force to at least one of the levers such that once the finger slides over the at least one of the teeth, the engaging side is in contact with that tooth.

9. The disposable bidirectional ratchet according to claim 2, wherein when the pins are in a third location, the pins do not apply a force to the levers.

10. The disposable bidirectional ratchet of claim 1, wherein said hollow elongated member of said toggle comprises a distal end with rib catches and a proximal end comprising a flat surface supporting said plurality of pins.

* * * * *